US00PP31930P2

(12) United States Plant Patent
Koning

(10) Patent No.: US PP31,930 P2
(45) Date of Patent: Jun. 30, 2020

(54) ***LAVANDULA* PLANT NAMED 'ANOUK DELUXE 108'**

(50) Latin Name: *Lavandula stoechas*
Varietal Denomination: Anouk Deluxe 108

(71) Applicant: Lammert Koning, Nuis (NL)

(72) Inventor: Lammert Koning, Nuis (NL)

(73) Assignee: L. Koning Beheer B.V., Nuis (NL)

( * ) Notice: Subject to any disclaimer, the term of this patent is extended or adjusted under 35 U.S.C. 154(b) by 0 days.

(21) Appl. No.: 16/501,649

(22) Filed: May 16, 2019

(51) Int. Cl.
*A01H 5/02* (2018.01)
*A01H 6/50* (2018.01)

(52) U.S. Cl.
USPC ..... Plt./445
CPC ..... *A01H 6/502* (2018.05)

(58) Field of Classification Search
USPC ..... Plt./445
CPC ..... A01H 6/502; A01H 5/02
See application file for complete search history.

*Primary Examiner* — Keith O. Robinson
(74) *Attorney, Agent, or Firm* — C. A. Whealy

(57) ABSTRACT

A new and distinct cultivar of *Lavandula* plant named 'Anouk Deluxe 108', characterized by its compact and upright plant habit; freely branching growth habit; freely flowering habit; dark violet-colored flowers and purple violet-colored terminal flower bracts positioned on strong and erect peduncles; long flowering period; and good post-production and garden performance.

2 Drawing Sheets

Botanical designation: *Lavandula stoechas.*
Cultivar denomination: 'ANOUK DELUXE 108'.

BACKGROUND OF THE INVENTION

The present invention relates to a new and distinct *Lavandula* plant, botanically known as *Lavandula stoechas*, commonly referred to as Lavender and hereinafter referred to by the name 'Anouk Deluxe 108'.

The new *Lavandula* plant is a product of a planned breeding program conducted by the Inventor in Nuis, The Netherlands and Boskoop, The Netherlands. The objective of the breeding program was to develop new unique *Lavandula* plants with good performance and attractive plant form and flower coloration.

The new *Lavandula* plant originated from an open-pollination in May, 2013 of *Lavandula stoechas* 'Anouk', disclosed in U.S. Plant Pat. No. 16,685, as the female, or seed, parent with an unknown proprietary selection of *Lavandula stoechas* as the male, or pollen, parent. The new *Lavandula* plant was discovered and selected by the Inventor as a single flowering plant within the progeny of the stated open-pollination in a controlled environment in Nuis, The Netherlands in May, 2014.

Asexual reproduction of the new *Lavandula* plant by terminal cuttings in a controlled greenhouse environment in Boskoop, The Netherlands since August, 2014 has shown that the unique features of this new *Lavandula* plant are stable and reproduced true to type in successive generations.

SUMMARY OF THE INVENTION

Plants of the new *Lavandula* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of the new *Lavandula* plant. These characteristics in combination distinguish 'Anouk Deluxe 108' as a new and distinct *Lavandula* plant:

1. Compact and upright plant habit.
2. Freely branching growth habit.
3. Freely flowering habit.
4. Dark violet-colored flowers and purple violet-colored terminal flower bracts positioned on strong and erect peduncles.
5. Long flowering period.
6. Good postproduction and garden performance.

Plants of the new *Lavandula* differ primarily from plants of the female parent, 'Anouk', in the following characteristics:

1. Plants of the new *Lavandula* are more compact and denser than plants of 'Anouk'.
2. Plants of the new *Lavandula* have a stronger reflowering habit than plants of 'Anouk'.
3. Plants of the new *Lavandula* have dark violet-colored flowers and purple violet-colored terminal flower bracts whereas plants of 'Anouk' have purple violet-colored flowers and violet-colored terminal flower bracts.

Plants of the new *Lavandula* can be compared to plants of the *Lavandula stoechas* 'Silver Anouk', disclosed in U.S. Plant Pat. No. 20,068. In side-by-side comparisons, plants of the new *Lavandula* differ primarily from plants of 'Silver Anouk' in the following characteristics:

1. Plants of the new *Lavandula* are more compact and denser than plants of 'Silver Anouk'.
2. Plants of the new *Lavandula* have a stronger reflowering habit than plants of 'Silver Anouk'.
3. Plants of the new *Lavandula* have dark violet-colored flowers and purple violet-colored terminal flower bracts whereas plants of 'Silver Anouk' have dark violet-colored flowers and purple-colored terminal flower bracts.

Plants of the new *Lavandula* can be compared to plants of the *Lavandula stoechas* 'Toscane', disclosed in U.S. Plant Pat. No. 18,046. In side-by-side comparisons, plants of the new *Lavandula* differ primarily from plants of 'Toscane' in the following characteristics:

1. Plants of the new *Lavandula* are more compact and denser than plants of 'Toscane'.
2. Plants of the new *Lavandula* have a stronger reflowering habit than plants of 'Toscane'.
3. Plants of the new *Lavandula* have dark violet-colored flowers and purple violet-colored terminal flower bracts whereas plants of 'Toscane' have purple-colored flowers and light violet-colored terminal flower bracts.

BRIEF DESCRIPTION OF THE PHOTOGRAPHS

The accompanying photographs illustrate the overall appearance of the new *Lavandula* plant showing the colors as true as it is reasonably possible to obtain in colored reproductions of this type. Colors in the photographs may differ slightly from the color values cited in the detailed botanical description which accurately describe the colors of the new *Lavandula* plant.

The photograph on the first sheet is a side perspective view of a typical flowering plant of 'Anouk Deluxe 108' grown in a container.

The photograph on the second sheet is a close-up view of a typical flowering plant of 'Anouk Deluxe 108'.

DETAILED BOTANICAL DESCRIPTION

Plants used in the aforementioned photographs and following detailed description were grown in 12-cm containers during the spring and early summer in an outdoor nursery in Boskoop, The Netherlands and under cultural practices typical of commercial *Lavandula* production. Plants were pinched one time and were ten months old when the photographs and description were taken. During the production of the plants, day temperatures ranged from 10° C. to 30° C. and night temperatures ranged from 5° C. to 20° C. In the following description, color references are made to The Royal Horticultural Society Colour Chart, 2015 Edition, except where general terms of ordinary dictionary significance are used.

Botanical classification: *Lavandula stoechas* 'Anouk Deluxe 108'.

Parentage:

*Female, or seed, parent.*—*Lavandula stoechas* 'Anouk', disclosed in U.S. Plant Pat. No. 16,685.

*Male, or pollen, parent.*—Unknown proprietary selection of *Lavandula stoechas*, not patented.

Propagation:

*Type.*—Terminal vegetative cuttings.

*Time to initiate roots, summer and winter.*—About ten days at temperatures about 18° C.

*Time to produce a rooted young plant, summer.*—About 60 days at temperatures about 20° C.

*Time to produce a rooted young plant, winter.*—About 70 days at temperatures about 20° C.

*Root description.*—Fine, fibrous; initially white in color and becoming more brown with development; actual color of the roots is dependent on substrate composition, water quality, fertilizer type and formulation.

*Rooting habit.*—Freely branching; dense.

Plant description:

*Plant and growth habit.*—Herbaceous perennial; compact and upright plant habit; flattened globular plant shape; freely branching habit; moderately vigorous growth habit; moderate growth rate; flowers arranged in verticillasters on crowded spikes with showy terminal flower bracts.

*Plant height, soil level to top of foliar plane.*—About 14.8 cm.

*Plant height, soil level to top of floral plane.*—About 20 cm.

*Plant width.*—About 21.7 cm.

*Lateral branch description.*—Quantity per plant: About nine primary lateral branches each with about eight secondary lateral branches developing per plant. Length: About 4.7 cm. Diameter: About 1.25 mm. Internode length: About 9 mm. Strength: Moderately strong. Aspect: About 35° from vertical. Texture and luster: Densely tomentose; matte. Color, when developing: Close to 145A; pubescence, close to 157D. Color, developed: Close to 144C; pubescence, close to 157D.

*Leaf description.*—Arrangement: Opposite, simple; sessile. Length: About 2.8 cm. Width: About 4 mm. Shape: Narrowly oblanceolate, flat. Apex: Bluntly acute. Base: Cuneate. Margin: Entire; slightly to moderately revolute; not lobed. Texture and luster, upper surface: Moderately to densely tomentose; matte. Texture and luster, lower surface: Moderately tomentose; matte. Fragrance: Strongly aromatic, pungent. Venation pattern: Pinnate. Color: Developing leaves, upper and lower surfaces: Close to 138B. Fully expanded leaves, upper surface: Close to NN137D; venation, close to 138A; pubescence, close to 157D. Fully expanded leaves, lower surface: Close to 137B; venation, close to 138B; pubescence, close to 157D.

Flower description:

*Flower type, arrangement and habit.*—Small single salverform flowers arranged in compact verticillasters on crowded terminal spikes; freely flowering, about 170 flowers developing per inflorescence and more than 5,000 flowers developing per plant; flowers with two-lobed upper lip and three-lobed lower lip; flowers face mostly outwardly on the spike; inflorescences with showy terminal flower bracts.

*Natural flowering season.*—Long flowering period; continuous from late spring into late summer in The Netherlands; strong reflowering habit; plants begin flowering about 13 weeks after planting.

*Flower longevity on the plant.*—Individual flowers last about four weeks on the plant; flowers not persistent.

*Fragrance.*—None detected.

*Flower buds.*—Length: About 5 mm. Diameter: About 1.5 mm. Shape: Elliptic. Texture and luster: Moderately tomentose; matte. Color: Close to 145B; distally, tinged with close to 143B to 143C; at the apex, close to N92C; pubescence, close to NN155D.

*Inflorescence size.*—Height: About 6.1 cm. Diameter, at terminal flower bracts: About 2.9 cm. Diameter, below flower bracts: About 1.8 cm.

*Flower size*.—Diameter: About 4.5 mm by 5 mm. Depth (height): About 9.5 mm. Throat diameter: About 1 mm. Tube length: About 6 mm. Tube diameter: About 1 mm.

*Petals*.—Quantity and arrangement: Upper lip, two-lobed and lower lip, three-lobed. Length, upper lip: About 9 mm. Length, lower lip: About 8 mm. Width, upper lip: About 1.5 mm. Width, lower lip: About 1.5 mm. Shape: Roughly spatulate; lower 72.5% fused into a tube. Apex: Obtuse, rounded. Margin: Entire; slightly undulate. Texture and luster, upper surface: Smooth, glabrous; velvety; matte. Texture and luster, lower surface: Smooth, glabrous; velvety; slightly glossy. Color: When opening, upper and lower surfaces: Close to N92A. Fully opened, upper and lower surfaces: Close to 86A; venation, close to 86A; color becoming closer to N92A with development. Throat: Close to 86A; venation, close to 86A. Tube: Close to 86B to 86C fading proximally to close to N155D; venation, close to 86B to 86C fading proximally to close to N155D.

*Terminal flower bracts*.—Quantity and arrangement: About six positioned upright at inflorescence apex. Length: About 2.2 cm. Width: About 9 mm. Shape: Obovate to narrowly obovate. Apex: Obtuse. Base: Narrowly cuneate. Margin: Entire; slightly undulate. Texture and luster, upper and lower surfaces: Slightly tomentose; matte. Color, upper surface: Close to N81B; main vein, close to N186B; pubescence, close to NN155D. Color, lower surface: Close to N81B; main vein, close to 187A; pubescence, close to NN155D.

*Basal flower bracts*.—Quantity and arrangement: Each group of seven flowers is subtended by a single basal flower bract. Length: About 9 mm. Width: About 9 mm. Shape: Broadly rhomboidal. Apex: Broadly aristate. Base: Cuneate. Margin: Entire. Texture and luster, upper surface: Smooth, glabrous; matte. Texture and luster, lower surface: Densely tomentose; matte. Color, upper surface: Close to 148A tinged with close to 200D; venation, close to 143A. Color, lower surface: Close to 177A; venation, close to 200A; pubescence, close to NN155D.

*Sepals*.—Quantity and arrangement: Five, fused into a campanulate tube. Length: About 5.5 mm. Width: About 0.75 mm. Shape: Lanceolate. Apex: Acute. Margin: Entire. Texture and luster, upper and lower surfaces: Densely pubescent; matte. Color: When opening and fully opened, upper surface: Proximally, close to 145D; distally, tinged with close to 145A; pubescence, close to NN155D. When opening and fully opened, lower surface: Proximally, close to 145B; distally, tinged with close to 143B to 143C; pubescence, close to NN155D.

*Peduncles*.—Length: About 4.7 cm. Diameter: About 2 mm. Aspect: Mostly upright. Strength: Strong. Texture and luster: Densely tomentose; matte. Color: Close to 138B; pubescence, close to NN155D.

*Reproductive organs*.—Stamens: Quantity per flower: Four. Filament length: About 1 mm. Filament color: Close to 85C. Anther shape: Reniform. Anther size: About 0.75 mm by 0.75 mm. Anther color: Close to 202A. Pollen amount: Moderate. Pollen color: Close to 13A. Pistils: Quantity per flower: One. Pistil length: About 4 mm. Stigma shape: Club-shaped. Stigma diameter: About 0.5 mm. Stigma color: Close to N92A. Style length: About 3.5 mm. Style color: Close to NN155D. Ovary color: Close to 143B to 143C.

*Seeds and fruits*.—To date, seed and fruit production has not been observed on plants of the new *Lavandula*.

Pathogen & pest resistance: To date, plants of the new *Lavandula* have not been noted to be resistant to pathogens and pests common to *Lavandula* plants.

Garden performance: Plants of the new *Lavandula* have exhibited good tolerance to rain and wind and have been observed to tolerate high temperatures about 40° C. and to be suitable for USDA Hardiness Zones 7 to 10.

It is claimed:

1. A new and distinct *Lavandula* plant named 'Anouk Deluxe 108' as illustrated and described.

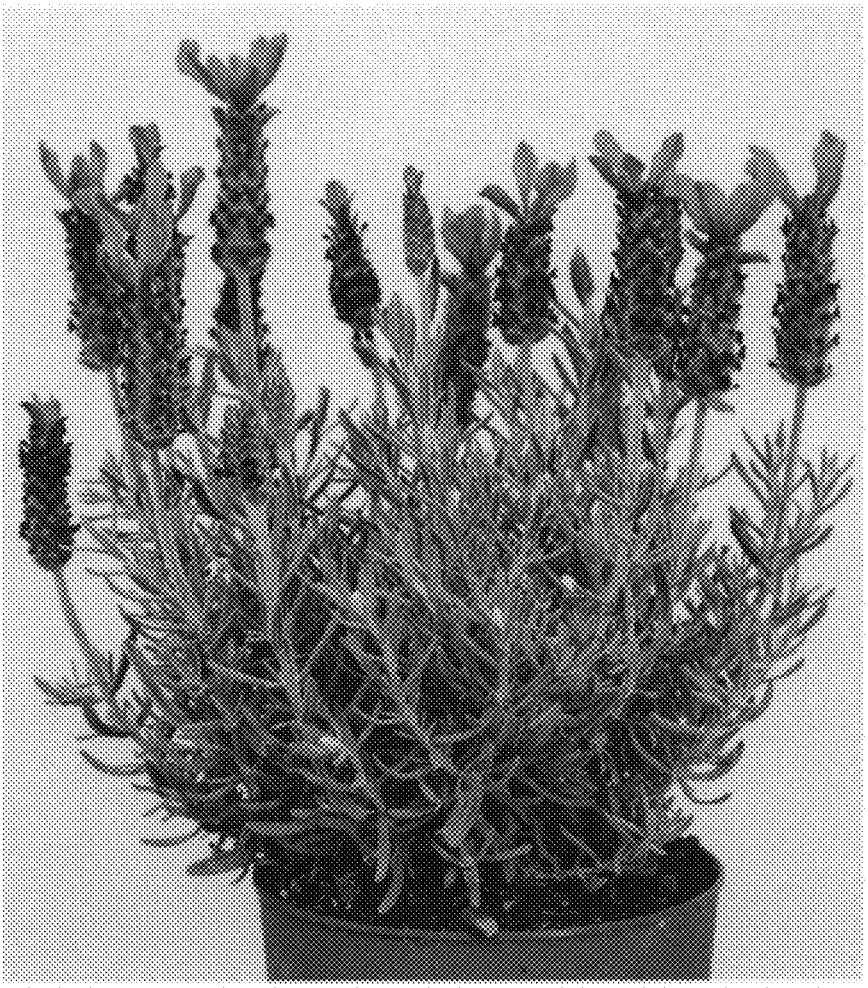

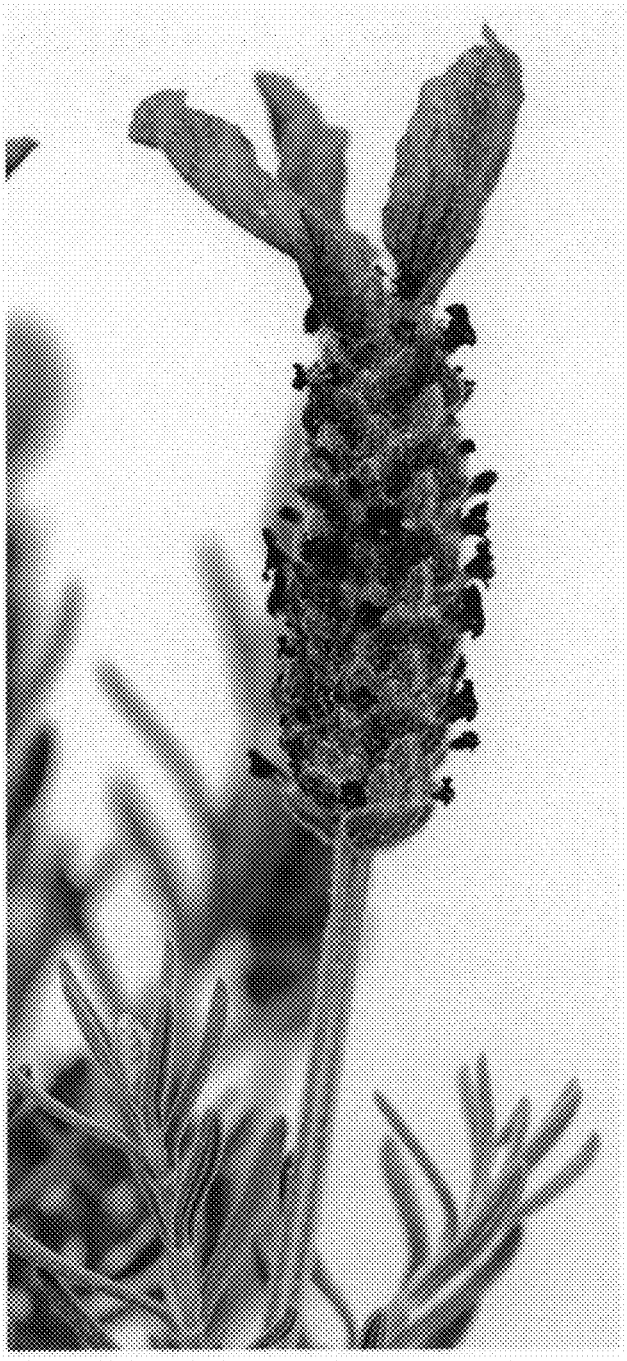

* * * * *